United States Patent [19]
Bergmann et al.

[11] Patent Number: 5,639,670
[45] Date of Patent: Jun. 17, 1997

[54] DETERMINATION OF FREE THYROID HORMONES BY COMPETITIVE IMMUNOASSAY

[75] Inventors: Andreas Bergmann; Joachim Struck, both of Berlin, Germany

[73] Assignee: B.R.A.H.M.S. Diagnostica GmbH, Berlin, Germany

[21] Appl. No.: 325,409

[22] PCT Filed: Apr. 22, 1993

[86] PCT No.: PCT/EP93/00981

§ 371 Date: Jan. 17, 1995

§ 102(e) Date: Jan. 17, 1995

[87] PCT Pub. No.: WO93/22675

PCT Pub. Date: Nov. 11, 1993

[30] Foreign Application Priority Data

May 6, 1992 [DE] Germany ............. 42 14 922.3

[51] Int. Cl.$^6$ ................................. G01N 33/53
[52] U.S. Cl. ............ 436/578; 435/7.1; 435/7.92; 435/7.93; 435/7.94; 435/7.95; 435/96; 435/962; 435/968; 435/971; 435/975; 435/500; 435/538; 435/539; 435/540; 435/543; 435/808; 435/817; 435/822; 435/824
[58] Field of Search ................. 435/7.1, 7.92, 435/7.93, 7.94, 7.95, 961, 962, 968, 971, 975; 436/500, 518, 538–540, 543, 808, 817, 822, 824

[56] References Cited

U.S. PATENT DOCUMENTS

| | | | |
|---|---|---|---|
| H0001018 | 1/1992 | Hantke | 436/500 |
| 4,366,143 | 12/1982 | Midgley et al. | 436/501 |
| 4,839,299 | 6/1989 | Charlton et al. | 436/500 |
| 5,278,080 | 1/1994 | Midgley et al. | 436/500 |
| 5,304,498 | 4/1994 | Ekins | 436/501 |

FOREIGN PATENT DOCUMENTS

| | | | |
|---|---|---|---|
| 0089806 | 9/1983 | European Pat. Off. | |
| 0106615 | 4/1984 | European Pat. Off. | |
| 0 161 107 | 11/1985 | European Pat. Off. | 436/518 |
| 0161107 | 11/1988 | European Pat. Off. | |
| 2744835 | 4/1978 | Germany | |
| 8303306 | 9/1983 | WIPO | |
| 8500226 | 1/1985 | WIPO | |
| 8911655 | 11/1989 | WIPO | |

*Primary Examiner*—Carol A. Spiegel
*Attorney, Agent, or Firm*—Cushman Darby & Cushman Intellectual Property Group of Pillsbury Madison & Sutro, LLP

[57] ABSTRACT

A method is revealed for the quantitative determination of the proportion of the free form of a thyroid hormone ligand in a sample of a biological fluid in which the ligand is present partly in the free form and also partly in a form in which it is bound to physiological binding proteins. In the first step, a ligand derivative of the thyroid hormone with an immunoglobulin, a labelled specific binder, and a test tube whose walls are coated with an excess of a protein material are provided. In the second step, a sample of the biological fluid containing an unknown amount of the free thyroid hormone ligand, a solution containing a known amount of the ligand derivative, and a solution containing a known, less than stoichiometric amount of the labelled specific binder are added to the test tube to form a liquid reaction mixture. In the third step, the reaction mixture is incubated to allow the free thyroid hormone ligand and the ligand derivative in the liquid reaction mixture to compete for the binding sites of the labelled specific binder, and to allow, in a concomitant slower reaction, the binding of the immunoglobulin part of the ligand derivative to the excess of the protein material on the walls of the test tube. In the fourth step, the remaining liquid reaction mixture is removed from the test tube. In the final steps, the amount of labelled specific binder bound to the walls of the test tube is determined and the amount of the free thyroid hormone ligand calculated.

9 Claims, 4 Drawing Sheets

DETERMINATION OF FREE THYROID HORMONES BY COMPETITIVE IMMUNOASSAY

The present invention relates to a method for the determination of the amount of a ligand in a sample of a biological fluid, in which the biological fluid containing the ligand to be determined is incubated in the presence of a dissolved ligand derivative, which can be converted into an insoluble form, in the liquid phase with less than the stoichiometric amount of a labelled specific binder which binds both the ligand to be determined and the ligand derivative so that the ligand to be determined and the ligand derivative compete for the labelled specific binder, and in which the ligand derivative is converted into an insoluble form and, after separation of the insoluble components of the assay system from those components of the assay system remaining in the liquid phase, the amount of the ligand to be determined in the biological fluid is calculated from the amount of the labelled specific binder bound to the ligand derivative, and a kit for carrying out such a method.

The present invention relates in particular to a method of the stated type for the determination of the free portion of a monovalent ligand, i.e. of a ligand which represents a monovalent antigen or a hapten, which is to say that it has only one binding site for the immunological binding by a specific binding partner, namely a thyroid hormone, which is present in biological fluids partly in a form bound to its physiological binding proteins and partly in unbound, i.e. free, form, and the object of the process is the quantitative determination of this free proportion.

The method according to the invention is one of the immunological assay methods in which labelled antibodies (labelled specific binders) are employed and which are also referred to as immunometric assay methods. It belongs to the version of such methods which is referred to as a competitive method. In contrast to typical sandwich methods, in which the total amount of the ligand to be determined is bound in a sandwich, a proportion of the labelled binding partner is bound to the ligand to be determined and a further proportion to a competing derivative of this ligand. Further statements on various types of immunometric assay methods are to be found in the introduction of EP-B-89806 in which, exactly as in EP-B-103605, the immunometric version of a method for the determination of free proportions of ligands is described, which method is described as the so-called analogue tracer assay method in EP-B-26103.

In immunometric methods of the type according to the invention for the determination of the free proportions of ligands, in particular monovalent ligands such as the thyroid hormones, the ligand to be determined and the ligand derivative taken in a known amount are allowed to compete for a minor amount of the labelled antibodies according to the above description of the fundamental method on which the present invention is based. The labelled antibody is bound essentially completely to the free ligand and the ligand derivative, and its distribution over the two binding partners reflects the concentration to be determined of the ligand in the sample. In order to obtain information about the concentration to be determined for the ligand and the distribution of the labelled antibody over the ligand to be measured and the ligand derivative, the reaction product of ligand derivative and labelled antibody is preferably immobilised for separation from the remaining assay solution, which, according to EP-P-103605, is effected by converting the ligand derivative into an insoluble form before or after incubation with the labelled antibody. In practice, the procedure generally adopted to date is to initially take the ligand derivative from the outset in a form immobilised by binding to the solid substrate.

Embodiments of a method of this type are described in EP-A-303284 and EP-A-324540.

In a version of the method of the stated type, which version is described in EP-A-149631, an exogenous binder for the ligand derivative is used in addition to the conventional components of the assay method. This exogenous binder for the ligand derivative may be an additional antibody specific to the latter. Its function should be to form a sort of buffer for the ligand derivative. Since, in the method discussed in EP-A-149631, the ligand derivatives are chemically modified ligands and have hapten character and are therefore monovalent, in the method according to EP-A-149631 the exogenous binder does not bind, with immobilisation, the complex formed in the determination and consisting of ligand derivative and labelled antibody.

In another method for the determination of free substances according to EP-A-106615, a specific binder is used which simultaneously binds to the ligand to be determined and to an antibody for the specific binder, and the binding of the ligand and the binding of the additional antibody should influence one another so that there is competition between the two and it is possible to derive the concentration of the free ligand to be determined from the extent of binding of the antibody.

If, in methods according to EP-B-89806 or EP-B-103605 or EP-A-303284 or EP-A-324540, immobilised ligand derivatives which compete with the free ligand to be determined for the labelled antibody are used, problems ("matrix effects") are frequently encountered in practice and are due to the fact that the reaction between the immobilised ligand derivative and the labelled antibody are reactions at the surface of the solid phase where diffusion processes play an important role and which are considerably determined by certain random properties of the solid phase. In practice, these matrix effects mean that the individual production batches of solid substrates with the immobilised ligand derivatives must all be carefully tested for their properties, with the frequent occurrence of high percentages of useless substrates which have to be separated as waste and which considerably increase the costs of the production process and therefore also of the final assay method.

EP-A-105 714 furthermore discloses that, in typical immunometric sandwich methods in which a polyvalent ligand, such as, for example, TSH, is completely bound by reaction with two different antibodies, the required incubation times can be shortened by carrying out the actual sandwich formation as a liquid-phase reaction and then extracting the sandwich formed from the reaction system by adding a solid phase having a binding partner for one of the sandwich antibodies. This method is suitable only for the determination of the total concentration of a ligand which has at least two binding sites for specific binding partners.

It is an object of the present invention to provide a rapid and reliable method for the determination of the amount of a free ligand in a sample of a biological fluid according to the precharacterising clause of Patent Claim 1, which can be carried out rapidly, reliably and with high accuracy and in which the matrix problems described above, which adversely affect the cost-efficiency of the conventional corresponding methods, are avoided.

This object is achieved with a method according to the precharacterising clause of Patent Claim 1 by the measures stated in the characterising clause of this Claim.

Advantageous and preferred embodiments of a process of this type and a kit which serves for realising the method are described in the subclaims.

The procedure adopted in the method according to the invention is such that the competing reaction of the free ligand to be determined and of the ligand derivative with the labelled antibody takes place in the liquid phase in the presence of a protein material which is bound to a solid phase and which specifically binds the substrate protein part of a ligand derivative used as a conjugate in a reaction which is slower than the actual immune reaction and leads to a non-covalent protein bond, and thus extracts the immune complex comprising ligand derivative and labelled antibody from the liquid reaction mixture.

In the method according to the invention, at the end of the reaction the labelled antibody bound to the ligand derivative is bound as part of a sandwich structure via the ligand derivative, its substrate protein part and the immobilised protein material to the solid substrate. In contrast to conventional sandwich methods, what is therefore bound is the ligand derivative used in a predetermined amount and not the ligand to be determined. In the case of monovalent ligands, such as monovalent antigens or haptens, such as, for example, the thyroid hormones, it is usually not possible to produce a sandwich structure. This is, however, permitted in accordance with a method as disclosed in EP-A-161 107 by the use of a soluble ligand derivative in the form of a conjugate of a ligand with a substrate protein. The presence of the free ligand to be determined is evident as a disturbance of the synthesis of the stated sandwich structure, in that those parts of labelled antibodies which are bound by the free ligand are not immobilised on the solid phase but remain in solution and therefore provide information about the amount of the ligand to be determined.

In the present application—and, for example, also in EP-A-303284 —a derivative of the ligand, in which the latter or a chemically modified form thereof is covalently bonded to a protein substrate molecule, is defined as a conjugate of a ligand.

By using a ligand derivative which is a conjugate of the ligand with a sterically bulky substrate protein, the ligand derivative is simultaneously a "differentially binding ligand derivative" in the meaning of the prior art described at the outset, which derivative has considerably reduced binding capability compared with physiological binding proteins and hence permits trouble-free determination of the free proportion of a ligand to be determined.

The labelled antibody used in the method according to the invention is preferably a monoclonal antibody which has such affinity properties with respect to the free ligand to be determined and the ligand derivative that it is bound to both to an extent which reflects the amount of the free ligand to be determined, and different affinities may be capable of compensating for the effect of relatively large concentration differences of the two binding partners. In the case of the determination of free thyroxine (FT4), for example, a monoclonal antibody having an association constant of the order of $10^{10}$ l/mol is suitable.

The ligand derivative is as a rule used in an amount which is of the order of 0.5 to 20 times the molar amount, based on the amount of the ligand to be determined which is to be expected in a sample from a normal patient. The labelled antibody is used in an amount which is less than the stoichiometric amount based on the sum of the amount of the ligand to be determined which is to be expected in the sample and the known added amount of the ligand derivative.

The method according to the invention is described in detail below, taking as an example a preferred embodiment in the form of a coated tube test method for the determination of free thyroxine (FT4) in the serum. In this method, a constant, predetermined amount of a T4-IgG conjugate (L-IgG) and free T4 (L) from the sample compete in the solution for a constant amount of labelled anti-T4 antibody (tracer; Ak*). Immobilised on the tube walls is an anti-IgG antibody (anti-IgG) which binds the $T_4$-IgG conjugate and hence, as part of the immune complex comprising ligand derivative and tracer, also the tracer part which is not bound by the fractions of free $T_4$ present in the sample and is therefore no longer available for binding to the $T_4$-IgG conjugate. The measurement is thus based on an $FT_4$ concentration-dependent disturbance of the immunometric determination of a constant amount of a $T_4$ derivative by sandwich formation.

The labelled antibody can be labelled with any of the known labels or label systems which are listed in detail, for example, in the prior art publications discussed at the outset. In particular, it can be labelled with a known radioactive isotope, in particular an iodine isotope, and the assay method is then an immunoradiometric assay method. The labelled component can, however, also be another known label, for example an enzyme or a fluorescent or, preferably, a chemiluminescent label.

The method according to the invention is illustrated in detail below for a preferred embodiment with reference to the Figures.

Figure 1:
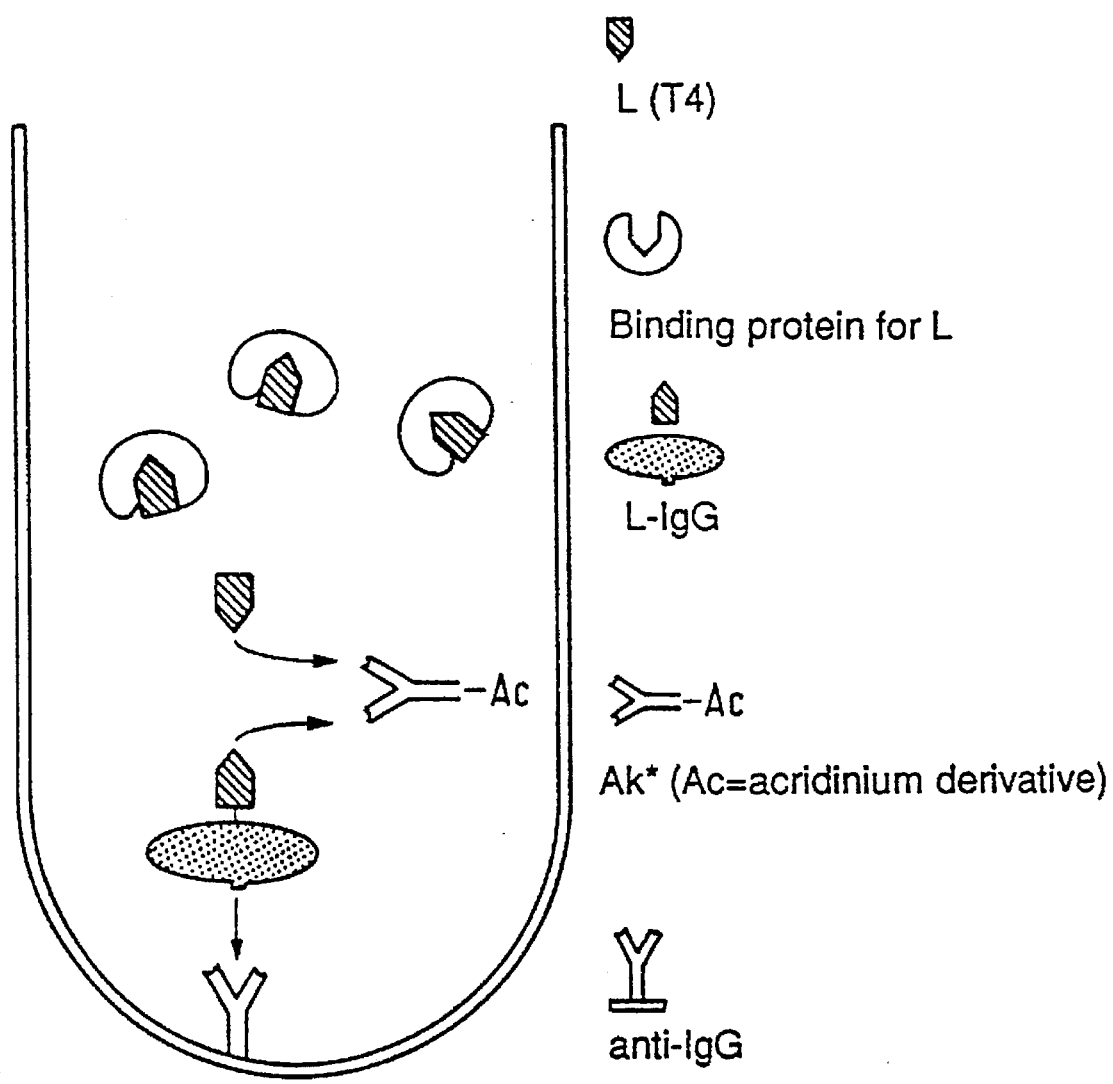
FIG. 1 shows a schematic representation of the test principle.

In the method described as the preferred embodiment, according to the generally valid scheme shown in FIG. 1, the serum sample containing the ligand to be determined, a $T_4$ rabbit IgG conjugate solution and a solution containing labelled anti-$T_4$ antibodies are pipetted immediately in succession into a test tube coated with goat anti-rabbit antigens. The labelled anti-$T_4$ antibody is preferably a monoclonal antibody and cross-reacts neither with the substrate protein part of the $T_4$-IgG conjugate nor with the coating of the test tube. $FT_4$ from the sample thus competes with the $T_4$ rabbit IgG conjugate as the ligand derivative for a labelled specific binder in the form of a labelled anti-$T_4$ antibody, in a homogeneous liquid-phase reaction. At the same time, but more slowly, $T_4$ rabbit IgG conjugate is bound to the immobilised goat anti-rabbit antibody and—inversely proportionally to the $FT_4$ content of the serum sample—conjugate-bound, labelled anti-$T_4$ antibody. After incubation for two hours, the test tube is washed and the labelled antibody remaining in the tube is measured on the basis of its labelling.

Since the decisive competitive reaction in the liquid phase takes place substantially more rapidly than the liquid-solid phase reaction, this method according to the invention does not have the fundamental kinetic problems of a corresponding method in which a $T_4$ conjugate immobilised at the outset is employed.

For the described version of the method according to the invention, in the preparation of the $T_4$ rabbit IgG conjugate used as a ligand derivative, it is necessary to ensure the immunological recognition of said conjugate both with respect to the $T_4$ part by the labelled antibody and with respect to the IgG part for immobilisation by production of a sandwich.

This requirement can be met, for example, if, as in the Example below, the $T_4$ rabbit IgG conjugate used as the ligand derivative is obtained by a gentle method in which the substrate protein is not significantly denatured or which permits isolation of conjugates with a natural, nondenatured protein moiety.

EXAMPLE a) Preparation of a $T_4$ rabbit IgG conjugate

Figure 2A:
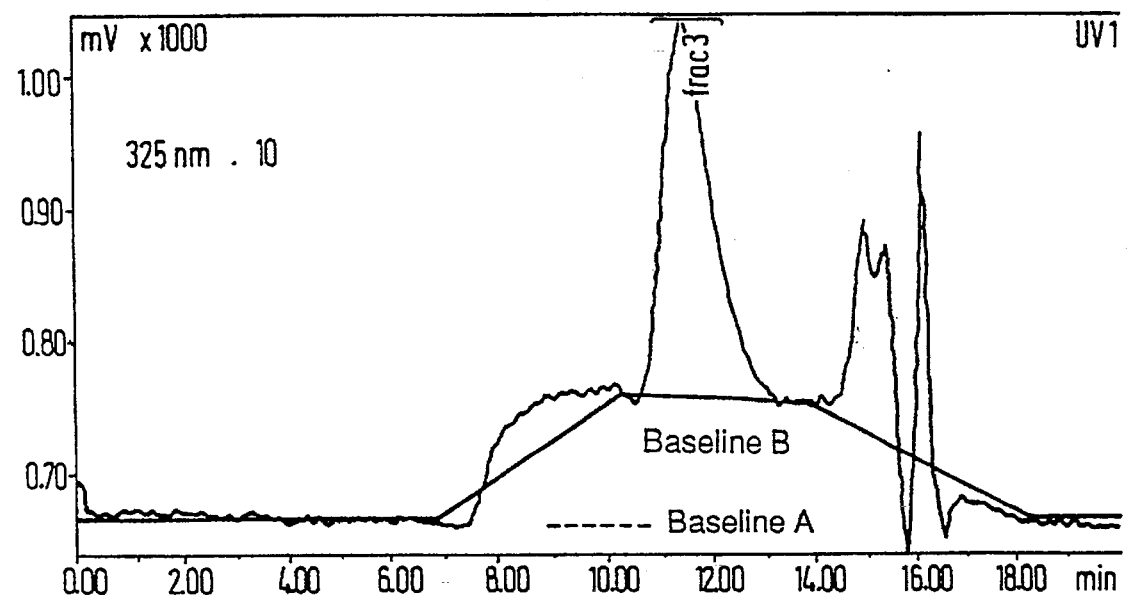
FIG. 2 shows an elution profile of an HPLC gel chromatography of a reaction mixture for preparation of the $T_4$-IgG conjugate used as the ligand derivative in a preferred embodiment of the method according to the invention, the natural $T_4$-IgG conjugate used in the Examples described below being eluted at 11 minutes.
Figure 2B:
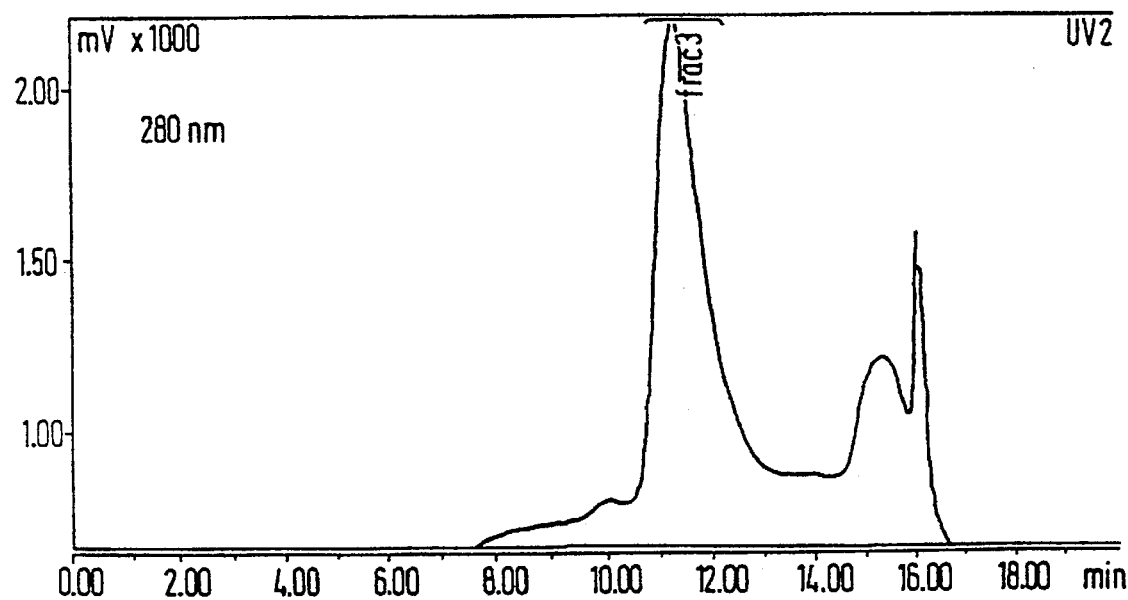

34μg of $T_4$-NHS active ester (Henning Berlin) in 50 μl of acetonitrile are incubated with 1 mg of rabbit IgG (SIGMA) in 0.5 ml of phosphate buffer, pH 8.0, for 90 minutes at room temperature. Natural rabbit IgG reacted with $T_4$-NHS active ester is isolated by HPLC gel chromatography and thus separated from $T_4$-IgG aggregates, unreacted $T_4$-NHS active ester and other reaction products. The example of an elution profile is shown in FIG. 2. The $T_4$-IgG loading is determined by means of a multichannel UV absorption detector continuously measuring the column flow, through measurement of the absorbance at 325 and 280 nm during the chromatography.

In the determination, the amount of $T_4$ rabbit IgG conjugate per determination which is used in the test is the maximum of 20 times the (molar) amount of FT4 in a sample in a normal patient (about 20 pmol/l).

b) Preparation of a labelled anti-$T_4$ antibody

As a labelled specific binder, a monoclonal anti-$T_4$ antibody obtained in a manner known per se is labelled by a known reaction with an acridinium ester as a chemiluminescent label. The labelled antibody is used in the test method in a substoichiometric amount relative to the $T_4$ rabbit IgG conjugate and relative to $FT_4$. Luminescent labelling of the antibody is carried out as follows:

10 μg of acridinium ester in 10 μl of acetonitrile (Hoechst Behring) are incubated with 100 μg of monoclonal anti-$T_4$ antibody (Henning Berlin) in 90 μl of phosphate buffer, pH 8.0, for 20 minutes. The labelled antibody is then purified by hydroxyapatite chromatography. About 110,000 RLU (measured with an Autoclinilumat from Berthold) of the labelled antibody are used per determination.

c) Preparation of the test tubes coated with the protein material

The tubes used in the test are prepared by coating suitable polystyrene tubes with 2.5 μg of goat anti-rabbit IgG (SCANTIBODIES)/0.5 ml of 0.1M $NaHCO_3$, pH 8.0, for 24 hours at room temperature. This is followed by decanting, washing with water and subsequent coating for two hours with 3% solution of a sorbitol syrup in which crystallisation has been suppressed (trade mark Karion), 0.5% of BSA and 0.005% of $NaN_3$. Decanting is carried out again and the tubes are freeze-dried for storage for subsequent use.

d) Assay procedure

Figure 3:
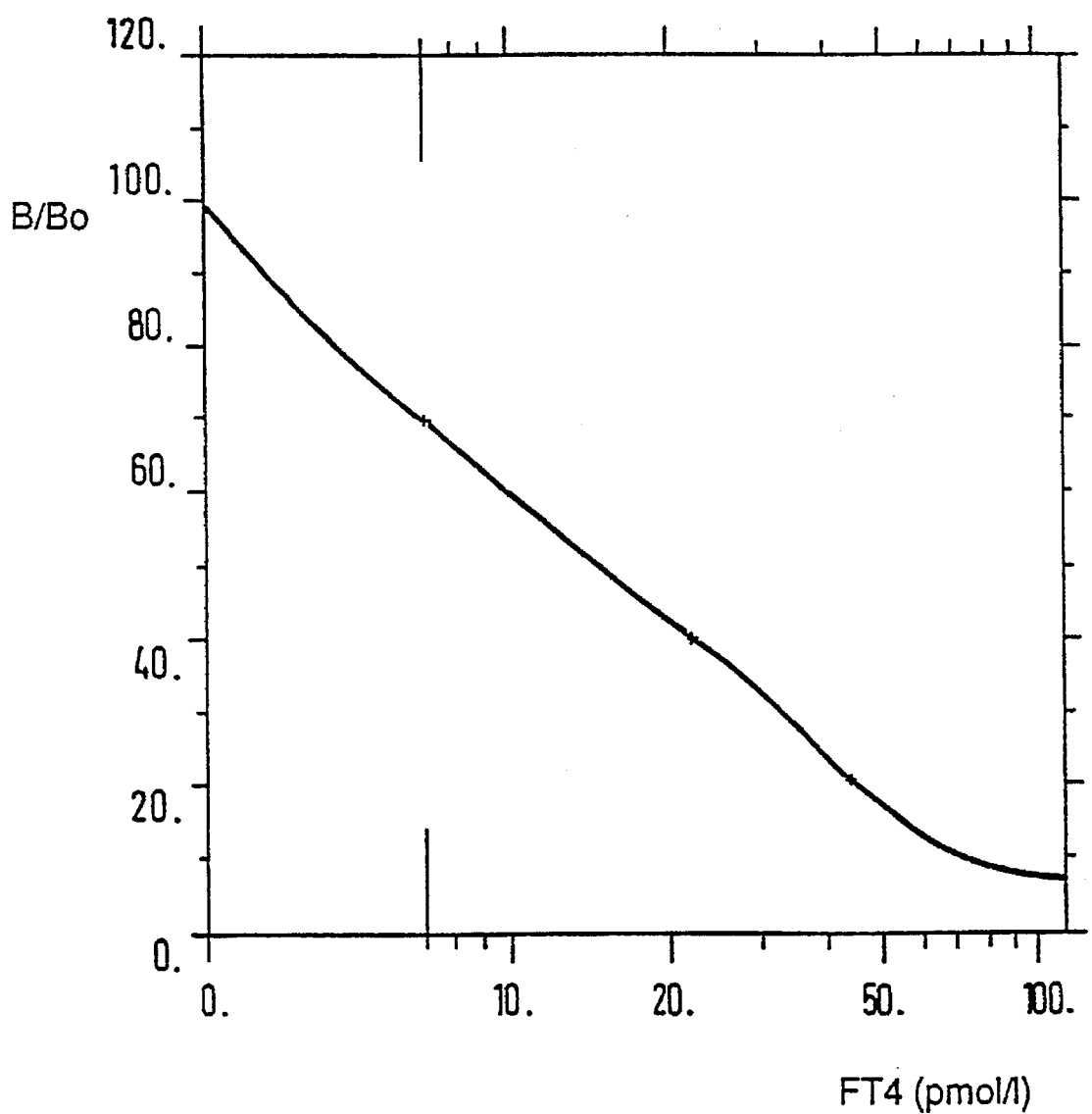
FIG. 3 shows a typical standard curve for the method according to the invention for the determination of $FT_4$.

The test is carried out as follows, using the components prepared above under a) to c):

The following are pipetted immediately in succession per tube: 50 μl of serum sample or standard, 200 μl of $T_4$-IgG conjugate solution, 200 μl of solution containing labelled antibody. The two last-mentioned solutions contain 50 mM HEPES, pH 7.4, 150 mM NaCl, 0.1% gelatine and 0.05% $NaN_3$. The tubes are incubated for 2 hours while shaking at 170 rpm. Finally, the tubes are each washed with 4×1 ml of wash solution and are measured in a luminometer. The following results illustrated by FIGS. 3 and 4 are obtained:

FIG. 3 shows the average standard curve of the method described, which curve results from the determination of the inter-assay variation of the test.

Figure 4:
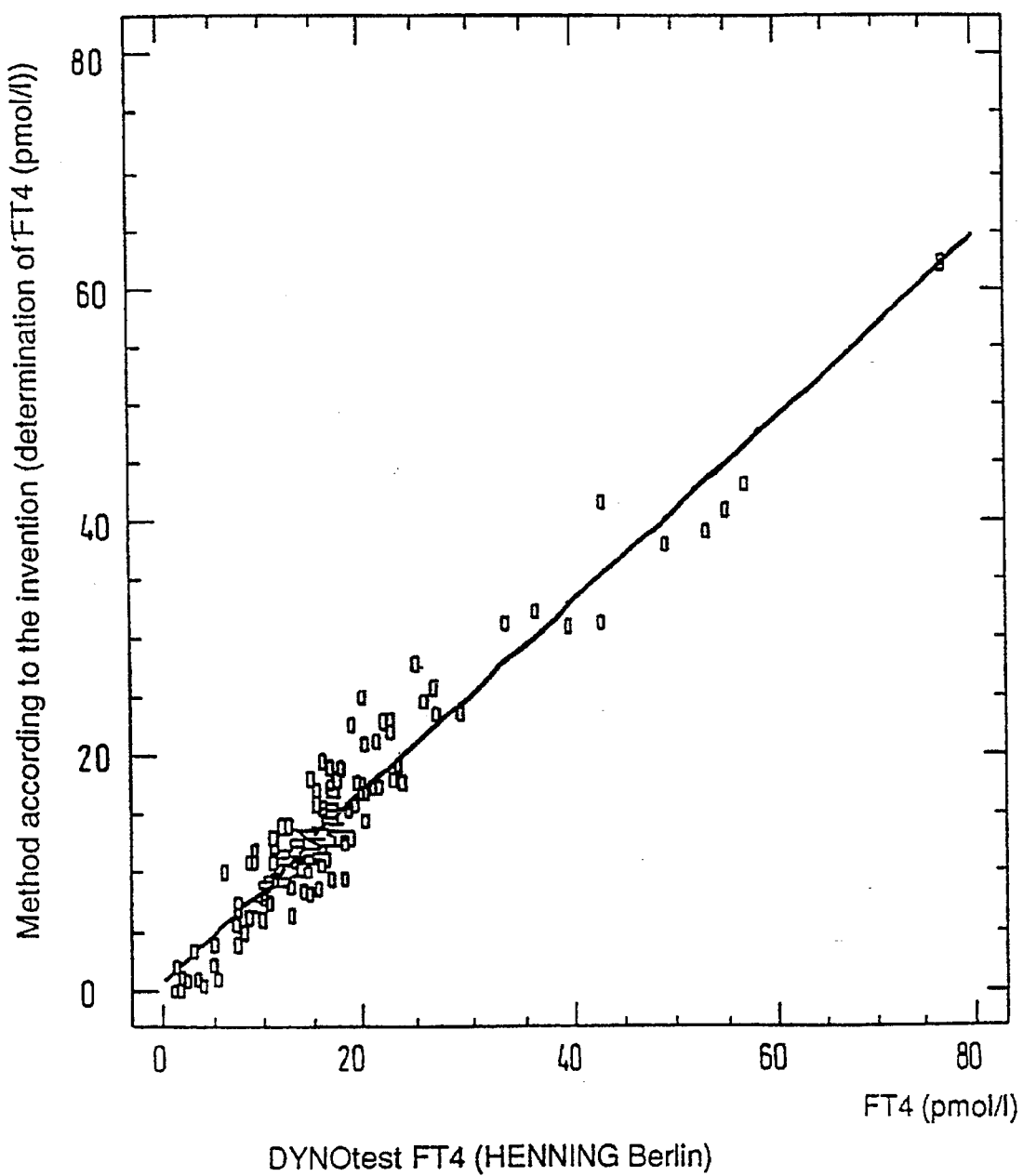
FIG. 4 shows a comparison of the results of the method according to the invention with those of a commercially available assay method for $FT_4$ (DYNOtest $FT_4$ from Henning Berlin).

FIG. 4 shows the correlation, obtained with 189 patient sera, between the test according to the invention and a known commercial test (DYNOtest $FT_4$ from Henning Berlin). The evaluation using a computer program gave a coefficient of 0.96. The line of best fit was calculated as follows:

($FT_4$ test according to the invention; pmol/l)=0.8× (DYNOtest FT4; pmol/l)+1.1 pmol/l.

e) Further testing of the effect of certain assay parameters on the assay method e1) Effect of the variation of the amount of $T_4$ rabbit IgG conjugate used at various $T_4$-IgG loading levels:

Four different $T_4$-IgG conjugates were synthesised and purified, and the $T_4$ loading was determined by measuring the absorbances at 325 nm and 280 nm. Table 1 below shows that only very small amounts of conjugate are required in order to achieve binding of the tracer in the $FT_4$ test according to the invention.

TABLE 1

| Conjugate # | $T_4$-IgG loading level 325 nm/280 | Amount of conjugate per determination | % $B_oT$ |
| --- | --- | --- | --- |
| 1 | 3.9 10E-2 | 20 ng | 49 |
| 1 | 3.9 10E-2 | 5 ng | 19 |
| 1 | 3.9 10E-2 | 1 ng | 5 |
| 2 | 2.3 10E-2 | 20 ng | 32 |
| 2 | 2.3 10E-2 | 5 ng | 11 |
| 2 | 2.3 10E-2 | 1 ng | 3 |
| 3 | 1.5 10E-2 | 20 ng | 21 |
| 3 | 1.5 10E-2 | 5 ng | 7 |
| 3 | 1.5 10E-2 | 1 ng | 2 |
| 4 | 1.1 10E-2 | 20 ng | 15 |
| 4 | 1.1 10E-2 | 5 ng | 5 |
| 4 | 1.1 10E-2 | 1 ng | 2 | e2) Testing of the stability of the test tubes used in the $FT_4$ test according to the invention and coated with anti-rabbit IgG:

The change in the quality of the tubes due to storage was tested by incubation with $^{125}$I-labelled rabbit IgG and the same amount of $^{125}$I-labelled rabbit IgG which had been diluted with an excess of unlabelled rabbit IgG. Table 2 below shows the binding found in the presence of the unlabelled rabbit IgG, based on the binding of the undiluted $^{125}$I-labelled rabbit IgG, and the coefficient of variance of 50 determinations of this binding.

TABLE 2

| Storage after production | % binding + IQG addition, based on binding without IgG addition | % CV (50 times) |
| --- | --- | --- |
| 1 day | 45.4 | 2.4 |
| 5 weeks, 4° C. | 45.3 | 2.1 |
| 5 weeks, 37° C. | 43.6 | 1.8 |

The results show that the tubes have very high stability—even at elevated storage temperatures. These stabilities are considerably better than those of conventional test tubes on whose walls an immobilised $T_4$ derivative in the form of a $T_4$-IgG conjugate is present. In these known tubes, considerable changes occur after storage for only one week at 37° C., in comparison with the data for the freshly produced tubes. In contrast, the tubes to be used in the method according to the invention are stable over several weeks at 37° C.

We claim:

1. A method for the quantitative determination of the amount of free form of a thyroid hormone ligand in a sample of a biological fluid in which the ligand is present partly in the free form and also partly in a form in which it is bound to physiological binding proteins, comprising the steps of:
    a) providing
        (i) a ligand derivative in the form of a soluble conjugate of the thyroid hormone with an immunoglobulin, the ligand derivative having essentially no binding capability with respect to the physiological binding proteins,
        (ii) a labelled specific binder which in an immunological binding reaction specifically binds both the free thyroid hormone ligand and the ligand derivative, and
        (iii) test tubes whose walls are coated with an excess of a protein material which selectively binds the immunoglobulin part of the ligand derivative without affecting the binding between the thyroid hormone part of the ligand derivative and the labelled specific binder, the protein material being selected from anti-isotypic immunoglobulins and anti-isotypic poly- or monoclonal antibodies against the immunoglobulin part of the ligand derivative,
    b) adding to the test tubes
        i) a sample of the biological fluid containing an unknown amount of the free thyroid hormone ligand, or a standard solution of the thyroid hormone ligand,
        ii) a solution containing a known amount of the ligand derivative, and
        iii) a solution containing a known, less than stoichiometric amount of the labelled specific binder, to form a liquid reaction mixture;
    c) incubating the reaction mixture to allow the free thyroid hormone ligand and the ligand derivative in the liquid reaction mixture to compete for binding sites of the labelled specific binder, and to allow, in a concomitant slower reaction, binding of the immunoglobulin part of the ligand derivative to the excess of the protein material on the walls of the test tubes;
    d) removing remaining liquid reaction mixture from the test tubes;
    e) determining the amount of labelled specific binder bound to the walls of the test tubes; and
    f) calculating the amount of the free thyroid hormone ligand.

2. The method of claim 1, wherein the free thyroid hormone ligand to be determined is free thyroxine ($FT_4$), the ligand derivative is a thyroxine-IgG conjugate and the protein material bound to the walls of the test tubes is an anti-isotypic IgG.

3. The method of claim 2, wherein the ligand derivative is a thyroxine-rabbit IgG conjugate and the anti-isotypic IgG is a goat anti-rabbit IgG or a goat anti-rabbit antibody.

4. The method of claim 1, wherein the walls of the test tubes are coated with an amount of the protein material which is at least sufficient for completely binding the total amount of the ligand derivative used, wherein an amount of the ligand derivative used is between 0.5 to 20 times the molar amount of free thyroid hormone ligand expected in a normal patient, and wherein the labelled specific binder is used in a substoichiometric amount such that only a portion of the free ligand present in the sample and of the ligand derivative react with the labelled specific binder.

5. The method of claim 2, wherein said labelled specific binder is a labelled monoclonal antibody to $T_4$ which does not react neither with the immunoglobulin part of the ligand derivative nor the protein material.

6. The method of claim 1, wherein the immunoglobulin part of the ligand derivative is a native immunoglobulin.

7. The method of claim 1, which is carried out in the following sequence of incubation steps:
    a) adding to the test tubes the sample of the biological fluid, or the standard solution of the thyroid hormone ligand;
    b) adding a solution which contains the known amount of the ligand derivative; and
    c) adding the solution containing the known, less than stoichiometric amount of the labelled specific binder; and,
    d) after an adequate incubation period and removal of the liquid reaction mixture from the test tubes, washing the test tubes and determining the amount of free thyroid hormone ligand in the sample on the basis of proportion of labelled specific binder bound to the walls of the test tubes, referring to results obtained by same method for standard samples.

8. A kit for carrying out a method for quantitative determination of the amount of free form of a thyroid hormone ligand in a sample of a biological fluid, in which the ligand is present partly in the free form and also partly in a form in which it is bound to physiological binding proteins, which kit comprises, as separate reagents:
    i) a known amount of a ligand derivative in form of a soluble immunoglobulin conjugate of the thyroid hormone ligand,
    ii) a known amount of a labelled anti-ligand antibody,
    iii) test tubes whose walls are coated with an excess of an anti-isotypic immunoglobulin against the immunoglobulin part of the ligand derivative; and, optionally,
    iv) standard solutions containing known amounts of the thyroid hormone ligand to be determined, and
    v) buffer and dilution solutions.

9. The kit of claim 8, wherein the ligand derivative, the labelled anti-ligand antibody, the coating of the test tubes, and, optionally, the standard samples are present in freeze-dried form.

* * * * *